US008602974B2

(12) United States Patent
Goldwasser et al.

(10) Patent No.: US 8,602,974 B2
(45) Date of Patent: Dec. 10, 2013

(54) GASTROINTESTINAL TOOL OVER GUIDING ELEMENT (75) Inventors: Benad Goldwasser, Tel Aviv (IL); Oz Cabiri, Macabim (IL); Yossi Gross, Moshav Mazor (IL)

(73) Assignee: G.I. View Ltd., Ramat Gan (IL)

( * ) Notice: Subject to any disclaimer, the term of this patent is extended or adjusted under 35 U.S.C. 154(b) by 1151 days.

(21) Appl. No.: 11/813,457

(22) PCT Filed: Feb. 10, 2005

(86) PCT No.: PCT/IL2005/000178
§ 371 (c)(1),
(2), (4) Date: Sep. 26, 2007

(87) PCT Pub. No.: WO2006/072928
PCT Pub. Date: Jul. 13, 2006

(65) Prior Publication Data
US 2008/0167524 A1 Jul. 10, 2008

Related U.S. Application Data (63) Continuation-in-part of application No. 10/747,648, filed on Dec. 30, 2003, now abandoned, which is a continuation-in-part of application No. 10/639,442, filed on Aug. 13, 2003, now abandoned.

(60) Provisional application No. 60/642,245, filed on Jan. 6, 2005.

(51) Int. Cl.
*A61B 1/00* (2006.01)
*A61M 25/00* (2006.01)
*A61M 31/00* (2006.01)
*A61M 37/00* (2006.01)
*A61M 29/00* (2006.01)

(52) U.S. Cl.
USPC ..... 600/115; 600/585; 604/95.02; 604/95.03; 604/101.04; 606/197

(58) Field of Classification Search
USPC ............... 604/41, 42, 95.01, 95.03, 96.01, 604/103.06, 103.07, 104, 164.08–164.11, 604/275–279, 514; 600/114, 115, 433–435, 600/585; 606/192, 197
See application file for complete search history.

(56) References Cited

U.S. PATENT DOCUMENTS 3,895,637 A 7/1975 Choy
3,924,625 A 12/1975 Peterson
(Continued)

FOREIGN PATENT DOCUMENTS

DE 3630660 3/1988
EP 0242428 10/1987
(Continued)

OTHER PUBLICATIONS

U.S. Appl. No. 60/571,438.
(Continued)

*Primary Examiner* — Theodore Stigell
*Assistant Examiner* — Nathan R Price
(74) *Attorney, Agent, or Firm* — Frommer Lawrence & Haug LLP; William S. Frommer (57) ABSTRACT Gastrointestinal apparatus (10) is provided, including a guiding element (16) and an inflatable mechanical device (96), adapted to pull the guiding element (16) through a colon of a patient. A gastrointestinal tool (12) is shaped to define a bore (14) therethrough, and the guiding element (16) is adapted to pass through the bore (14). Other embodiments are also described.

30 Claims, 5 Drawing Sheets

(56) References Cited

U.S. PATENT DOCUMENTS

| | | |
|---|---|---|
| 4,040,413 A | 8/1977 | Ohshiro et al. |
| 4,066,070 A | 1/1978 | Utsugi |
| 4,077,610 A | 3/1978 | Masuda et al. |
| 4,445,892 A | 5/1984 | Hussein et al. |
| 4,530,698 A | 7/1985 | Goldstein et al. |
| 4,561,427 A | 12/1985 | Takada |
| 4,566,763 A | 1/1986 | Greguss et al. |
| 4,596,381 A | 6/1986 | Hamrick |
| 4,690,131 A | 9/1987 | Lyddy, Jr. et al. |
| 4,838,859 A | 6/1989 | Strassmann |
| 4,971,034 A | 11/1990 | Doi et al. |
| 4,976,524 A | 12/1990 | Chiba |
| 5,353,807 A | 10/1994 | DeMarco |
| 5,364,353 A | 11/1994 | Corfitsen et al. |
| 5,395,332 A | 3/1995 | Ressemann et al. |
| 5,398,670 A | 3/1995 | Ortiz et al. |
| 5,471,988 A | 12/1995 | Fujio et al. |
| 5,473,474 A | 12/1995 | Powell et al. |
| 5,509,371 A | 4/1996 | Phillips |
| 5,571,114 A | 11/1996 | Devanaboyina |
| 5,586,968 A | 12/1996 | Grundl et al. |
| 5,604,531 A | 2/1997 | Iddan et al. |
| 5,662,587 A | 9/1997 | Grundfest et al. |
| 5,728,068 A | 3/1998 | Leone et al. |
| 5,863,284 A | 1/1999 | Klein |
| 5,879,325 A | 3/1999 | Lindstrom et al. |
| 5,906,357 A | 5/1999 | Munson, Sr. |
| 5,906,591 A | 5/1999 | Dario et al. |
| 5,910,105 A | 6/1999 | Swain et al. |
| 5,941,815 A | 8/1999 | Chang |
| 5,984,860 A | 11/1999 | Shan |
| 6,007,482 A | 12/1999 | Madni et al. |
| 6,028,719 A | 2/2000 | Beckstead et al. |
| 6,071,234 A | 6/2000 | Takada |
| 6,130,783 A | 10/2000 | Yagi et al. |
| 6,157,018 A | 12/2000 | Ishiguro et al. |
| 6,277,065 B1 | 8/2001 | Donofrio |
| 6,315,713 B1 | 11/2001 | Takada |
| 6,332,865 B1 | 12/2001 | Borody et al. |
| 6,333,826 B1 | 12/2001 | Charles |
| 6,341,044 B1 | 1/2002 | Driscoll, Jr. et al. |
| 6,356,296 B1 | 3/2002 | Driscoll, Jr. et al. |
| 6,373,642 B1 | 4/2002 | Wallerstein et al. |
| 6,388,820 B1 | 5/2002 | Wallerstein et al. |
| 6,422,989 B1 | 7/2002 | Hektner |
| 6,424,377 B1 | 7/2002 | Driscoll, Jr. et al. |
| 6,439,032 B1 | 8/2002 | Lehmann et al. |
| 6,449,103 B1 | 9/2002 | Charles |
| 6,459,451 B2 | 10/2002 | Driscoll, Jr. et al. |
| 6,485,409 B1 | 11/2002 | Voloshin et al. |
| 6,493,032 B1 | 12/2002 | Wallerstein et al. |
| 6,503,192 B1 | 1/2003 | Ouchi et al. |
| 6,517,477 B1 | 2/2003 | Wendlandt |
| 6,527,705 B1 | 3/2003 | Ouchi |
| 6,537,206 B2 | 3/2003 | Takada |
| 6,544,276 B1 * | 4/2003 | Azizi ............................. 606/159 |
| 6,597,520 B2 | 7/2003 | Wallerstein et al. |
| 6,611,282 B1 | 8/2003 | Trubko et al. |
| 6,646,818 B2 | 11/2003 | Doi et al. |
| 6,648,814 B2 | 11/2003 | Kim et al. |
| 6,682,479 B1 | 1/2004 | Takahashi et al. |
| 6,695,771 B2 | 2/2004 | Takada et al. |
| 6,702,734 B2 | 3/2004 | Kim et al. |
| 6,704,148 B2 | 3/2004 | Kumata |
| 6,709,388 B1 | 3/2004 | Mosse et al. |
| 6,743,208 B1 | 6/2004 | Coyle |
| 6,764,441 B2 | 7/2004 | Chiel et al. |
| 6,786,864 B2 | 9/2004 | Matsuura et al. |
| 6,800,056 B2 | 10/2004 | Tartaglia et al. |
| 6,814,728 B2 | 11/2004 | Ouchi et al. |
| 6,824,510 B2 | 11/2004 | Kim et al. |
| 6,827,718 B2 | 12/2004 | Hutchins et al. |
| 6,837,846 B2 | 1/2005 | Jaffe et al. |
| 6,866,626 B2 | 3/2005 | Long et al. |
| 6,869,393 B2 | 3/2005 | Butler et al. |
| 6,911,005 B2 | 6/2005 | Ouchi et al. |
| 6,932,323 B2 | 8/2005 | James |
| 6,974,441 B2 | 12/2005 | Ravo et al. |
| 7,056,283 B2 | 6/2006 | Baror et al. |
| 2002/0012059 A1 | 1/2002 | Wallerstein et al. |
| 2002/0109772 A1 | 8/2002 | Kuriyama et al. |
| 2002/0109773 A1 | 8/2002 | Kuriyama et al. |
| 2003/0074015 A1 | 4/2003 | Nakao |
| 2003/0181788 A1 | 9/2003 | Yokoi et al. |
| 2003/0191369 A1 | 10/2003 | Arai et al. |
| 2003/0208219 A1 | 11/2003 | Aznoian et al. |
| 2003/0225433 A1 | 12/2003 | Nakao |
| 2004/0004836 A1 | 1/2004 | Dubuc |
| 2004/0111010 A1 | 6/2004 | Nishiie |
| 2004/0143161 A1 | 7/2004 | Baror et al. |
| 2004/0199087 A1 | 10/2004 | Swain et al. |
| 2004/0199088 A1 | 10/2004 | Bakos et al. |
| 2004/0199196 A1 | 10/2004 | Ravo |
| 2004/0204702 A1 | 10/2004 | Ziegler et al. |
| 2004/0249247 A1 | 12/2004 | Iddan |
| 2004/0260150 A1 | 12/2004 | Bernstein |
| 2005/0038317 A1 | 2/2005 | Ratnakar |
| 2005/0038319 A1 | 2/2005 | Goldwasser et al. |
| 2005/0095200 A1 | 5/2005 | Schwarzberg |
| 2005/0107664 A1 | 5/2005 | Kalloo et al. |
| 2005/0165272 A1 | 7/2005 | Okada et al. |
| 2006/0164733 A1 | 7/2006 | Gal et al. |
| 2006/0238879 A1 | 10/2006 | Togino |

FOREIGN PATENT DOCUMENTS

| | | |
|---|---|---|
| EP | 0267446 | 5/1988 |
| EP | 0659387 | 6/1995 |
| FR | 1465723 | 3/1967 |
| JP | 5-43114 | 6/1993 |
| JP | 7313443 | 12/1995 |
| JP | 10309259 | 11/1998 |
| JP | 2002031766 | 1/2002 |
| JP | 2006026344 | 2/2006 |
| WO | 00/44275 A1 | 8/2000 |
| WO | 0168540 | 9/2001 |
| WO | 02059676 | 8/2002 |
| WO | 02075348 | 9/2002 |
| WO | WO02068035 A1 | 9/2002 |
| WO | 03026272 | 3/2003 |
| WO | 03046830 | 6/2003 |
| WO | 03053225 | 7/2003 |
| WO | 2004008185 | 1/2004 |
| WO | 2004/016299 | 2/2004 |
| WO | 2004010858 | 2/2004 |
| WO | WO2004028354 A1 | 4/2004 |
| WO | WO-2004049905 | 6/2004 |
| WO | 2006/025045 | 3/2006 |

OTHER PUBLICATIONS

U.S. Appl. No. 60/607,986.

U.S. Appl. No. 60/652,049.

* cited by examiner

GASTROINTESTINAL TOOL OVER GUIDING ELEMENT

CROSS-REFERENCES TO RELATED APPLICATIONS

The present application is a U.S. national phase of PCT Application no. PCT/IL2005/000178, which: (a) claims priority from U.S. Provisional Patent Application 60/642,245, filed Jan. 6, 2005, entitled, "Gastrointestinal tool over guidewire"; and (b) is a continuation-in-part of U.S. application Ser. No. 10/747,648 to Goldwasser et al., filed Dec. 30, 2003, entitled, "Gastrointestinal tool over guidewire," which is a continuation-in-part of U.S. application Ser. No. 10/639,442 to Goldwasser, filed Aug. 13, 2003, entitled, "Gastrointestinal tool over guidewire." Each of these applications is assigned to the assignee of the present application and is incorporated herein by reference.

FIELD OF THE INVENTION

This invention relates generally to gastrointestinal tools, such as endoscopes and colonoscopes, and more particularly to gastrointestinal tools that slide over a guidewire, guiding catheter and the like, and which may be introduced into and through the colon, e.g., to the cecum, by any means.

BACKGROUND OF THE INVENTION

Endoscopy has become an increasingly important tool in diagnosing and in treating ailments of the gastrointestinal tract, also referred to as the GI tract. Typical endoscopes are essentially formed by a somewhat flexible tube that is pushed through the GI tract, after being introduced in the body cavity starting from the rectum or starting from the esophagus. The endoscope has a steerable tip to facilitate navigation through the GI tract, and typically has to be sufficiently stiff so that it can be pushed further along the body cavity. The tip of the endoscope that is introduced in the GI tract can be outfitted with several devices, most notably an illumination device and a vision device, such as a vision integrated circuit, so that the operator of the endoscope can observe the interior of the GI tract and maneuver the endoscope in the proper position.

Once the endoscope is in position, other tools attached to the endoscope or inserted through the endoscope can be brought to the proper position in the GI tract. Various procedures can then be carried out, such as removing polyps, performing sutures, irrigation, suction, and removing other tissues. The various tools that are used together with the endoscope can be either inserted separately in the GI tract and placed in the proper position independently, or may travel in a working channel of the endoscope, so that once the endoscope is positioned at the desired location in the GI tract, the tools inserted in the endoscope will also easily reach that position.

Endoscopes or other smaller similar devices can also be used to explore other body cavities, for example airways, genitourinary tract, female reproductive organs, etc., or blood vessels. These probes must be small to fit in the smaller cavities, and care must be taken to avoid damage to the more fragile membranes lining these cavities.

Current state of the art endoscopes are very capable devices, and endoscopy has been very successful in diagnostic and therapeutic applications with the use of current endoscopes and the current arsenal of tools that can be inserted through the working channel of the endoscope, or can be attached to the outside of the endoscope. However, current endoscope technology has limitations and drawbacks. One of the greatest drawbacks of current endoscopes is that the working channel is small. The working channel is small relative to overall diameter of the endoscope, and is further limited by the space taken up by vision, irrigation, suction, light, and control cabling mechanisms that are part of the endoscope and are required to control the endoscope. Thus there is a very small area left for other tools to be introduced through the endoscope. Also, the additional channels may make passage of the endoscope through body cavities more difficult, as they contribute among other things to its diameter.

U.S. Pat. No. 6,517,477 to Wendlandt, assigned to Scimed Life Systems, Inc. (Maple Grove, Minn., US), which is incorporated herein by reference, describes a catheter introducer system for endoscopy that includes a steering section and a propulsion section located near the end of the flexible, tubular catheter that is introduced in a body cavity. The propulsion section is designed to pull the rest of the catheter inside the body cavity, so there is no need to push the catheter along from outside the body. Propulsion may be accomplished by relatively movable gripping pads that selectively apply suction to the tissue. The steering section is designed to point the end of the catheter that is introduced into the body cavity in the desired direction. The catheter may be made very flexible in bending, and a larger diameter catheter may be used.

U.S. Pat. No. 6,800,056 to Tartaglia et al., which is incorporated herein by reference, describes an endoscope with guiding apparatus. A steerable endoscope is described having an elongate body with a manually or selectively steerable distal portion, an automatically controlled portion, a flexible and passively manipulated proximal portion, and an externally controlled and manipulatable tracking rod or guide. The tracking rod or guide is positioned within a guide channel within the endoscope and slides relative to the endoscope. When the guide is in a flexible state, it can conform to a curve or path defined by the steerable distal portion and the automatically controlled portion. The guide can then be selectively rigidized to assume that curve or path. Once set, the endoscope can be advanced over the rigidized guide in a monorail or "piggy-back" fashion so that the flexible proximal portion follows the curve held by the guide until the endoscope reaches a next point of curvature within a body lumen.

US Patent Application Publication 2004/0199087 to Swain et al., which is incorporated herein by reference, describes a method for inserting guide wires into a lumen, for example into the human gastrointestinal tract. A guide wire structure is employed which comprises at least two guide wires each having a leading end portion which terminates in a leading end, the guide wires being connected to one another by a junction at or adjacent their leading ends, the guide wires have a first position in which the leading end portions are substantially parallel to one another, a second position in which the leading end portions are curved, and a third position in which at least one of the leading end portions forms a loop. The guide wire structure is steered through the gastrointestinal tract by selectively advancing or retracting a single guide wire or advancing more than one guide wire simultaneously, according to the path which is required to be followed.

US Patent Application Publication 2004/0199088 to Bakos et al., which is incorporated herein by reference, describes a guide wire including a continuous, unitary wire having a first segment, a second segment, and a third segment. The third segment has a bending moment of inertia less than the bending moment of inertia of the first and second segments. The guide wire is described as being used to advance a medical device within a body lumen.

PCT Patent Publication WO 2004/010858 to Gross et al., which is incorporated herein by reference, describes an imaging system comprising an imaging device assembled on a carrier, and a first outwardly expandable element and a second outwardly expandable element mounted on the carrier, wherein the second expandable element is expandable both radially and axially, the imaging system comprising a mode of operation, wherein during expansion of the second expandable element, obstruction of the radial expansion of the second expandable element causes the axial expansion of the second expandable element to propel the carrier and the imaging device axially.

PCT Publication WO 99/40957 to Blume et al., which is incorporated herein by reference, describes a guide wire combined with a catheter or medical device for moving through a body lumen to a desired position in the body with the aid of an applied magnetic field. The guide wire is provided with a magnet on its distal end that is oriented or oriented and moved by the application of a magnetic field to the magnet. A catheter or other medical device is advanced over the guide wire. Once the medical device is in its desired position, the magnet may be withdrawn through the lumen of the catheter.

U.S. Pat. No. 6,837,846 to Jaffe et al., which is incorporated herein by reference, describes an endoscope that is slidably insertable within a lumen of a guide tube. The guide tube is configured to be rigidizable along its entire length from a relaxed configuration. The endoscope has a steerable distal portion to facilitate the steering of the device through tortuous paths. In the relaxed configuration, a portion of the guide tube is able to assume the shape or curve defined by the controllable distal portion of the endoscope. Having assumed the shape or curve of the endoscope, the guide tube may be rigidized by the physician or surgeon to maintain that shape or curve while the endoscope is advanced distally through the tortuous path without having to place any undue pressure against the tissue walls.

U.S. Pat. No. 6,827,718 to Hutchins et al., which is incorporated herein by reference, describes a steerable endoscope that uses rapid exchange technology, soft locks, and mechanical locks to maintain the position of the endoscope. Rapid exchange technology is used to minimize displacement forces present on the guidewire or catheters. Soft locks and mechanical locks are described as resisting movements caused by displacement forces.

U.S. Pat. No. 6,786,864 to Matsuura et al., which is incorporated herein by reference, describes an endoscope including a fixing member detachably mounted to a distal end portion of an endoscope insertion part for detachably fixing and holding a distal end portion of an indwelling tube or a distal end portion of a guide member for guiding the indwelling tube, both of which are provided along the axial direction of the insertion part, to the distal end portion of the insertion part.

U.S. Pat. No. 6,695,771 to Takada, which is incorporated herein by reference, describes a self-propelled colonoscope that is self-inserted into a colon by driving endless belts mounted on the outside of a bending section of an insertion tube. The cross section of the endless belt is substantially circular, and rack gear teeth having a circular cross section are formed on the outside of the endless belts.

U.S. Pat. No. 6,764,441 to Chiel et al., which is incorporated herein by reference, describes a self-propelled endoscope including expandable actuators surrounding a central conduit. Each actuator comprises a bladder that, when fluid is introduced, expands laterally while contracting longitudinally. A restorative spring can be placed inside a bladder and between the two ends to restore the actuator to its original shape as fluid is withdrawn. Multiple actuators can be placed in series to successively inflate and deflate and generate a peristaltic motion. One or more Shape Memory Alloy (SMA) springs can be affixed to one or more restorative springs to cause bending motion.

U.S. Pat. No. 6,702,734 to Kim et al., which is incorporated herein by reference, describes a self-propelled endoscopic micro-robot that is propelled through a tubular organ in forward and backward directions by an impact force generated within the robot by a propulsion piston that is moved within a cylinder of the robot by an alternating source of pressurized air.

US Patent Application 2004/0199087 to Swain et al., which is incorporated herein by reference, describes a guide wire structure that comprises at least two guide wires each having a leading end portion which terminates in a leading end, the guide wires being connected to one another by a junction at or adjacent their leading ends, the guide wires have a first position in which the leading end portions are substantially parallel to one another, a second position in which the leading end portions are curved, and a third position in which at least one of the leading end portions forms a loop. The guide wire structure is steered through the gastrointestinal tract by selectively advancing or retracting a single guide wire or advancing more than one guide wire simultaneously, according to the path which is required to be followed.

The following patent application publications, all of which are incorporated herein by reference, may be of interest:

US Patent Applications 2003/0225433 and 2003/0074015 to Nakao

US Patent Application 2004/0199196 to Ravo

US Patent Application 2004/0260150 to Bernstein

US Patent Application 2004/0204702 to Ziegler et al.

SUMMARY OF THE INVENTION

In some embodiments of the present invention, gastrointestinal apparatus is provided comprising an elongate guiding element; a mechanical device, adapted to pull the guiding element through a colon of a patient; and a gastrointestinal tool adapted to advance along the guiding element. For some applications, the tool is shaped so as to define a bore therethrough, and the guiding element is placed within the bore. For other applications, the tool comprises a coupling member, a portion of which is positioned adjacent to the tool and defines a bore through the coupling member. As the tool advances, successive portions of the guiding element are surrounded by the bore. In an embodiment, the coupling member is integral to the body of the tool. In another embodiment, the coupling member is attached to the tool.

The term "guiding element," as used in the specification and in the claims, encompasses any elongate element adapted to be introduced into a body lumen in order to facilitate the advancement of another element (such as a gastrointestinal tool, e.g., a colonoscope) into the body lumen, the guiding element including, but not limited to, such elements as a guidewire, a guiding catheter, a monorail, or a wire, which may or may not be hollow, and may or may not have segments, and may have any suitable material property (e.g., flexible, metallic, non-metallic). For some applications, the guiding element comprises a flexible (non-rigid, non-rigidizing) plastic tube, e.g., a plastic tube having a diameter of between about 4 mm and about 7 mm, such as about 5.5 mm. For some applications, when the guiding element comprises a monorail, the monorail is flexible such that it generally does not reshape the colon.

In some embodiments of the present invention, the gastrointestinal tool is adapted to be passively advanced along the guiding element, such as by being pushed by the physician. Alternatively, the tool is adapted to be actively advanced along the guiding element, such as by using an electrical element. For example, the tool may comprise a spinning gear, adapted to rotate while grasping the guiding element, thereby propelling the tool along the guiding element. For some applications, such a spinning gear is pneumatically or hydraulically powered.

In accordance with some embodiments of the present invention, the guiding element comprises a distal stop that prevents movement of the gastrointestinal tool therepast. Alternatively, for some applications, the guiding element does not comprise a distal stop. Further in accordance with some embodiments of the present invention, the gastrointestinal tool comprises an imaging device, such as but not limited to, a CCD camera, an illumination device, a vision device, an ultrasound sensor, and/or an x-ray emitter. Additionally or alternatively, the gastrointestinal tool comprises a cutting tool, a sampling device, and/or a magnetic device.

Still further in accordance with some embodiments of the present invention, the gastrointestinal tool comprises a catheter that advances along (e.g., over or alongside, as described above) the guiding element. For some applications, the catheter comprises a lumen for passing therethrough at least one of an instrument and a fluid. In accordance with an embodiment of the present invention, the gastrointestinal tool is shaped so as define a chamfer for facilitating passage through a lumen.

There is also provided, in accordance with some embodiments of the present invention, a method for constructing a gastrointestinal apparatus, comprising providing a guiding element, providing a mechanical device adapted to pull the guiding element through a colon of a patient, and providing a gastrointestinal tool adapted to pass along the guiding element. In addition, for some applications, another tool is provided that cooperates with the gastrointestinal tool, and is also adapted to be advanced along the guiding element. As another alternative, for some applications, a collapsible sleeve is adapted to be slid over the guiding element and inflated to functionally create an endoscope with single or multiple channels that run through its length.

There is thus provided, in accordance with an embodiment of the present invention, gastrointestinal apparatus including a guiding element, and a gastrointestinal tool including a coupling member formed with a bore, the guiding element passing through the bore. The gastrointestinal apparatus may include one or more of the following features. For example, the coupling member may be positioned inwards or outwards of an outer contour of the gastrointestinal tool. The gastrointestinal tool may include a radioactive device (e.g., at least one of a radioactive tube, radioactive needle, radioactive seed, and radioactive capsule), an iontophoresis drug delivery device, an injection device for injection of a substance, a photodynamic therapy/diagnosis device, a hyperthermic therapy/diagnosis device, an ultrasonic therapy/diagnosis device, and/or an imaging device.

A propulsion device may be adapted to propel the gastrointestinal tool along the guiding element. An anchoring device (e.g., an inflatable balloon) may be adapted to anchor the guiding element at a position in the gastrointestinal tract. Additionally or alternatively, the gastrointestinal tool may be coupled to a pulley.

There is therefore provided, in accordance with an embodiment of the present invention, gastrointestinal (GI) apparatus including:

a guiding element;

an inflatable mechanical device, adapted to pull the guiding element through a colon of a patient; and a gastrointestinal tool shaped to define a bore therethrough, the guiding element passing through the bore.

For some applications, the guiding element includes a distal stop that prevents movement of the gastrointestinal tool therepast. For some applications, the gastrointestinal tool is shaped to define a chamfer for facilitating passage through a lumen. For some applications, the gastrointestinal tool includes a cutting tool, a sampling device, and/or a magnetic device. For some applications, the guiding element has a diameter of at least 4 mm.

In an embodiment, the gastrointestinal tool includes an imaging device. For some applications, the imaging device includes at least one of: a CCD camera, a CMOS camera, an illumination device, a vision device, an ultrasound sensor, and an x-ray emitter.

In an embodiment, the gastrointestinal tool includes a catheter that slides over the guiding element. For some applications, the catheter includes a lumen for passing therethrough at least one of an instrument and a fluid.

In an embodiment, the gastrointestinal apparatus includes a biologically-compatible-fluid pressure source, and the inflatable mechanical device includes a piston head coupled to a distal portion of the guiding element and adapted to:

be inflated so as to form a pressure seal with a wall of the colon when the guiding element is in the colon, and be advanced distally through the colon in response to pressure from the fluid pressure source applied to an external surface of the piston head.

For some applications, the piston head is adapted to be in direct contact with the wall of the colon when the guiding element is in the colon. For some applications, the piston head is shaped to define a proximal lobe and a distal lobe, the lobes being in fluid communication with each other.

For some applications, the gastrointestinal apparatus is adapted to facilitate distal advancement of the piston head by facilitating passage of fluid out of the colon from a distal site within the colon distal to the piston head. For some applications, the gastrointestinal apparatus includes a vent tube, and the gastrointestinal apparatus is adapted to facilitate the passage of the fluid out of the colon from the distal site within the colon through the vent tube. For some applications, the vent tube is adapted to passively permit the passage of the fluid out of the colon from the distal site within the colon. For some applications, the vent tube is adapted to be coupled to a suction source, whereby to actively facilitate the passage of the fluid out of the colon from the distal site within the colon.

There is also provided, in accordance with an embodiment of the present invention, a method for constructing gastrointestinal apparatus, including:

providing a guiding element;

providing an inflatable mechanical device, adapted to pull the guiding element through a colon of a patient;

providing a gastrointestinal tool shaped to define a bore therethrough; and sliding the gastrointestinal tool over the guiding element, the guiding element passing through the bore.

For some applications, the method further includes sliding another tool over the guiding element that cooperates with the gastrointestinal tool. For some applications, the gastrointestinal tool includes an imaging device. For some applications, the gastrointestinal tool includes a catheter that slides over the guiding element. For some applications, the method further includes sliding a collapsible sleeve over the guiding element and inflating the sleeve to create an endoscope, the inflated sleeve including at least one channel.

There is further provided, in accordance with an embodiment of the present invention, gastrointestinal apparatus including:

a guiding element;

an inflatable mechanical device, adapted to pull the guiding element through a colon of a patient; and a gastrointestinal tool including a coupling member shaped to define a bore, the guiding element passing through the bore.

For some applications, the coupling member is positioned inwards of an outer contour of the gastrointestinal tool. Alternatively, for some applications, the coupling member is positioned outside an outer contour of the gastrointestinal tool.

For some applications, the gastrointestinal tool includes a radioactive device including at least one of a radioactive tube, radioactive needle, radioactive seed, and radioactive capsule.

For some applications, the gastrointestinal tool includes an iontophoresis drug delivery device, an injection device for injection of a substance, a photodynamic therapy/diagnosis device, a hyperthermic therapy/diagnosis device, an ultrasonic therapy/diagnosis device, and/or an optical biopsy device.

For some applications, the guiding element has a diameter of at least 4 mm.

For some applications, the gastrointestinal apparatus includes one or more clips, adapted to be clipped to the guiding element and the gastrointestinal tool, to facilitate sliding of the tool with respect to the guiding element.

For some applications, the gastrointestinal apparatus further includes a propulsion device adapted to propel the gastrointestinal tool along the guiding element. For some applications, the gastrointestinal apparatus includes a pulley, coupled to the gastrointestinal tool.

For some applications, the gastrointestinal tool includes an imaging device.

In an embodiment, the gastrointestinal tool is adapted to be actively advanced along the guiding element. For some applications, the gastrointestinal apparatus includes one or more wheels, adapted to create a functional engagement of the guiding element and the gastrointestinal tool, whereby to actively advance the tool along the guiding element.

In an embodiment, the gastrointestinal apparatus further includes an anchoring device adapted to anchor the guiding element at a position in a gastrointestinal tract. For some applications, the anchoring device includes an inflatable balloon.

In an embodiment, the gastrointestinal apparatus includes a biologically-compatible-fluid pressure source, and the inflatable mechanical device includes a piston head coupled to a distal portion of the guiding element and adapted to:

be inflated so as to form a pressure seal with a wall of the colon when the guiding element is in the colon, and be advanced distally through the colon in response to pressure from the fluid pressure source applied to an external surface of the piston head.

For some applications, the piston head is adapted to be in direct contact with the wall of the colon when the guiding element is in the colon. For some applications, the piston head is shaped to define a proximal lobe and a distal lobe, the lobes being in fluid communication with each other.

For some applications, the gastrointestinal apparatus is adapted to facilitate distal advancement of the piston head by facilitating passage of fluid out of the colon from a distal site within the colon distal to the piston head. For some applications, the gastrointestinal apparatus includes a vent tube, and the gastrointestinal apparatus is adapted to facilitate the passage of the fluid out of the colon from the distal site within the colon through the vent tube. For some applications, the vent tube is adapted to passively permit the passage of the fluid out of the colon from the distal site within the colon. Alternatively, the vent tube is adapted to be coupled to a suction source, whereby to actively facilitate the passage of the fluid out of the colon from the distal site within the colon.

There is still further provided, in accordance with an embodiment of the present invention, a method including:

inflating a mechanical device to pull a guiding element through a colon of a patient; and advancing a gastrointestinal tool along the guiding element.

For some applications, advancing the gastrointestinal tool includes causing the guiding element to pass through a bore defined by the gastrointestinal tool. Alternatively, for some applications, the gastrointestinal tool includes a coupling element, a portion of which is positioned adjacent to the tool and defines a bore therethrough, and advancing the gastrointestinal tool includes causing the guiding element to pass through the bore.

In an embodiment, pulling the guiding element includes pulling the guiding element to a vicinity of a furthest desired location of the gastrointestinal tool in the colon, and advancing the gastrointestinal tool includes advancing the gastrointestinal tool after the guiding element has been pulled to the vicinity of the desired location.

In an embodiment, the mechanical device includes a piston head, and inflating the mechanical device includes:

inflating the piston head to form a pressure seal between the piston head and a wall of the colon; and advancing the piston head distally through the body lumen by applying fluid pressure to an external surface of the piston head.

For some applications, advancing the piston head includes facilitating passage of fluid out of the lumen from a site within the lumen distal to the piston head. For some applications, forming the pressure seal includes placing the piston head in direct contact with the wall of the colon.

There is yet further provided, in accordance with an embodiment of the present invention, a method comprising:

mechanically pulling a guiding element through a colon of a patient until the guiding element reaches a vicinity of a furthest desired site in the colon; and advancing a gastrointestinal tool along the guiding element after the guiding element has been pulled to the vicinity of the desired location.

There is also provided, in accordance with an embodiment of the present invention, gastrointestinal (GI) apparatus including:

a guiding element;

a non-magnetically-driven device, adapted to pull the guiding element through a colon of a patient; and a gastrointestinal tool shaped to define a bore therethrough, the guiding element passing through the bore.

In an embodiment, the non-magnetically-driven device includes a device selected from the list consisting of: an electromechanical device, a mechanical device, and a device that uses suction to facilitate its advancement.

BRIEF DESCRIPTION OF THE DRAWINGS

The present invention will be understood and appreciated more fully from the following detailed description taken in conjunction with the appended drawings in which.

DETAILED DESCRIPTION OF PREFERRED EMBODIMENTS

Figure 1:
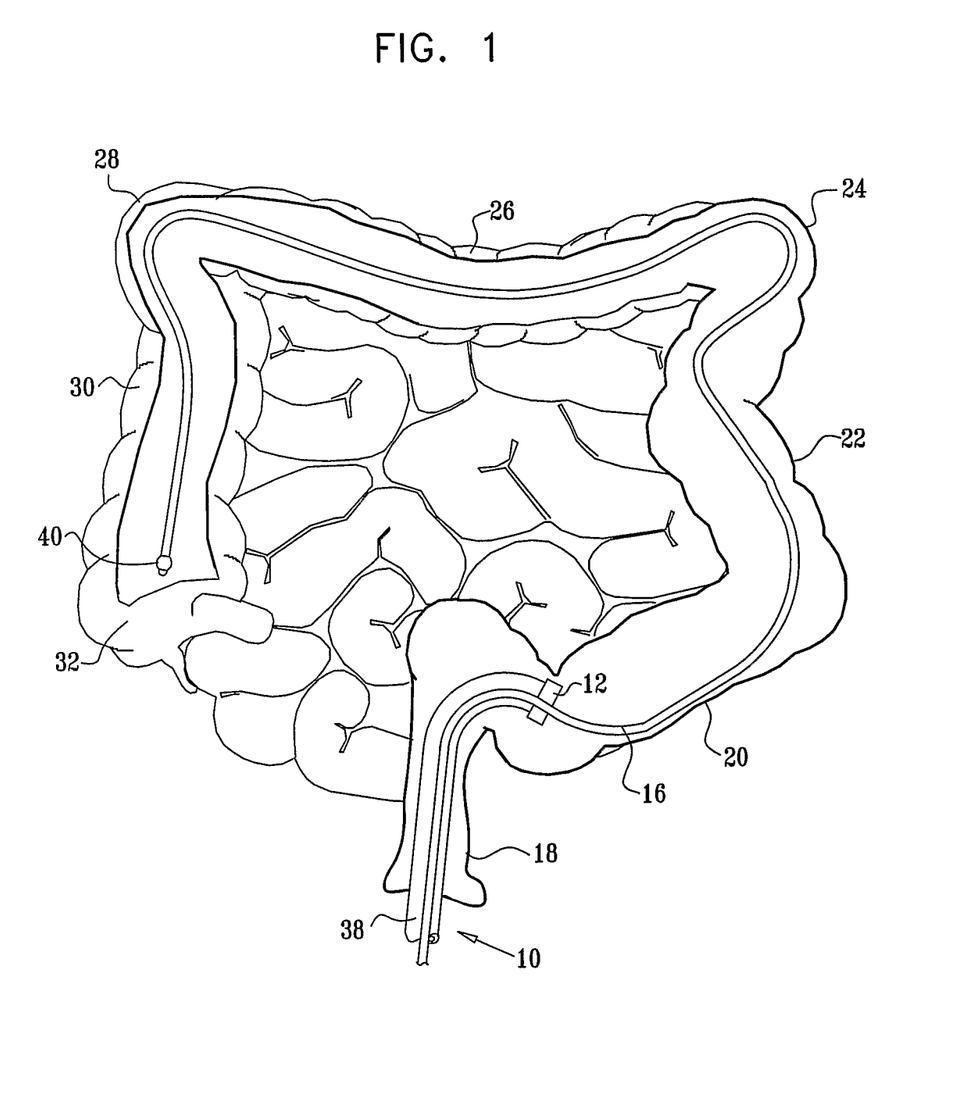
FIG. 1 is a simplified illustration of a guiding element, in accordance with an embodiment of the present invention, introduced through the rectum into the large intestine all the way to the cecum.
Figure 2:
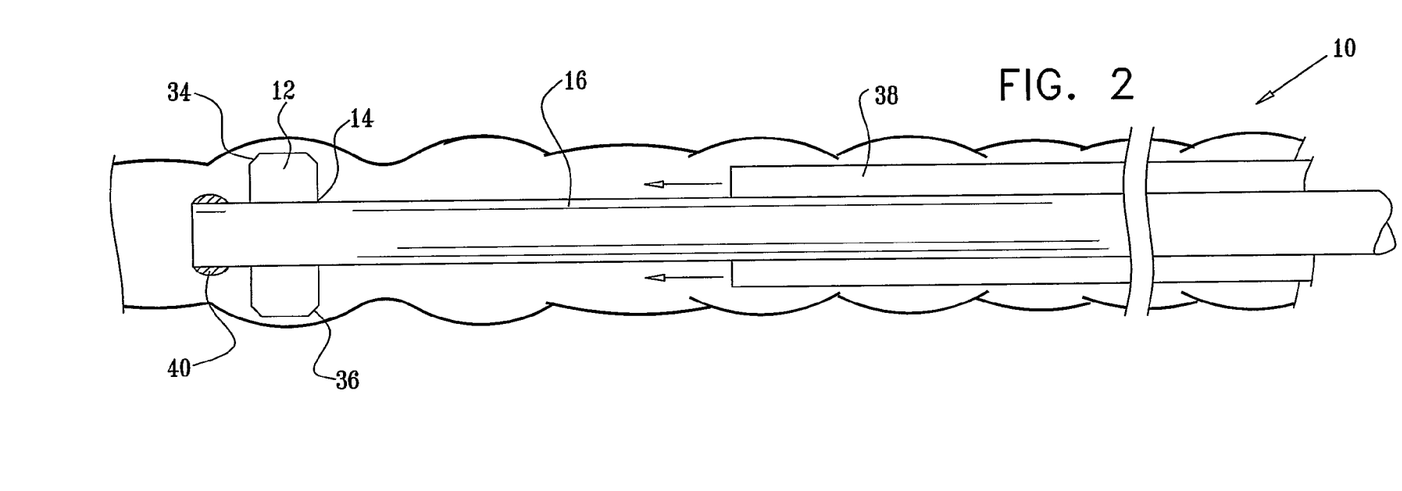
FIG. 2 is a simplified illustration of an imaging device and sleeve slid over the guiding element of FIG. 1, in accordance with an embodiment of the present invention.

Reference is now made to FIGS. 1 and 2, which illustrate gastrointestinal apparatus 10, constructed and operative in accordance with an embodiment of the present invention. Gastrointestinal apparatus 10 may comprise a gastrointestinal tool 12 formed with a bore 14 that advances over a guiding element 16. Guiding element 16 passes through bore 14. Examples of gastrointestinal tools 12 are described hereinbelow. Guiding element 16 may be constructed of any suitable flexible, medically safe material, such as a plastic or metal.

In the following description, guiding element 16 is described as being introduced into the gastrointestinal tract, particularly the colon. However, it is emphasized that the invention is not limited to the GI tract and may be used for any other body lumen.

As seen in FIG. 1, guiding element 16 may be introduced through a rectum 18, past a sigmoid colon 20 and descending colon 22, where it may bend past a splenic flexure 24, pass through a transverse colon 26, bend past a hepatic flexure 28, pass into an ascending colon 30, and reach a cecum 32, by any method.

Alternatively, guiding element 16 may be pulled through the colon, such as by a self-propelled mechanical device (or other devices, such as but not limited to, inflatable devices, electrical devices and the like). After guiding element 16 has been advanced through the colon, gastrointestinal tool 12 is then introduced into the colon along guiding element 16. Gastrointestinal tool 12 may be shaped so as to define a distal chamfer 34, e.g., to facilitate movement distally into the colon. Alternatively or additionally, gastrointestinal tool 12 may be shaped so as to define a proximal chamfer 36, e.g., to facilitate extraction from the colon.

In an embodiment of the present invention, the mechanical device comprises a guide member at least partially insertable into the anus, and an inflatable piston head mounted in a vicinity of a distal end of guiding element 16. The guide member is: (a) shaped so as to define a first passageway connectable to a source of fluid pressure, and (b) configured to permit sliding movement of guiding element 16 through the guide member.

The source of fluid pressure generates pressure in the colon proximal to the piston head, such that greater fluid pressure acting on a proximal side of the piston head than on a distal side of the piston head propels the piston head and the guiding element in a distal direction in the colon.

For some applications, a vent tube passes through the piston head. The vent tube is shaped so as to define an opening distal to the piston head through which fluid is vented to the outside of the body. For some applications, guiding element 16 is shaped so as to define a second passageway in fluid communication with the piston head, which passageway is connected to a source of fluid pressure for inflating the piston head.

For some applications, techniques described in U.S. patent application Ser. No. 10/967,922 Cabiri et al., filed Oct. 18, 2004, entitled, "Pressure-propelled system for body lumen," which is assigned to the assignee of the present application and is incorporated herein by reference, are used with the mechanical device, mutatis mutandis (including that the elongate carrier described therein comprises guiding element 16 of the present application).

In an embodiment of the present invention, a pushing device 38, such as but not limited to, a sleeve or catheter, is slid over guiding element 16 to distally push gastrointestinal tool 12 over guiding element 16. For some applications, guiding element 16 comprises a distal stop 40 that prevents distal movement of gastrointestinal tool 12 therepast. For some applications, distal stop 40 is inflatable, and is configured such that inflation of distal stop 40 fixes the position of guiding element 16 in the colon.

Alternatively, for some applications, guiding element 16 does not comprise distal stop 40. For some applications, after gastrointestinal tool 12 has been advanced along guiding element 16, the physician removes the guiding element from the colon. In embodiments in which gastrointestinal tool 12 is shaped so as to define bore 14, removal of guiding element 16 leaves the bore as a free working channel through which additional tools or materials can be advanced or withdrawn.

In accordance with an embodiment of the present invention, gastrointestinal tool 12 may comprise an imaging device. The imaging device may comprise, without limitation, a CCD or CMOS camera, an illumination device, a vision device, an ultrasound sensor, and/or an x-ray emitter.

Figure 3:
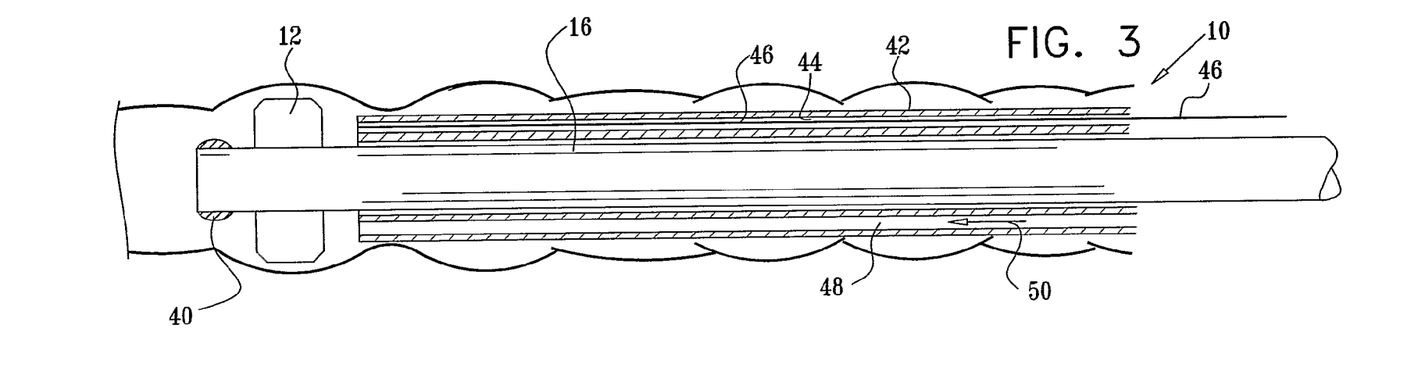
FIG. 3 is a simplified illustration of additional devices introduced over the guiding element of FIG. 1, such as, but not limited to, a catheter with a lumen for passing therethrough wires (electrical or other) and another lumen for introducing therethrough fluids, or other gastrointestinal tools and the like, in accordance with an embodiment of the present invention.

Reference is now made to FIG. 3, which is a simplified illustration of devices introduced over guiding element 16, in accordance with an embodiment of the present invention. For some applications, gastrointestinal tool 12 comprises a catheter 42 that slides over guiding element 16. Catheter 42 may comprise a lumen (also referred to as a channel) 44 for passing therethrough an instrument 46. Additionally or alternatively, catheter 42 may comprise a lumen (also referred to as a channel) 48 for passing therethrough a fluid 50. Catheter 42 may be rigid or flexible, and may have a one-piece or multiple-piece construction. Catheter 42 may comprise an inflatable, collapsible sleeve, as is described hereinbelow.

Catheter 42 may include any number of lumens for multiple applications. Catheter 42 may be constructed of any suitable medically safe material, such as plastic or metal.

Catheter 42 may have a generally fixed form, or may be made of a collapsible material (e.g., nylon), such that after partial or complete introduction into the body lumen, catheter 42 may be inflated to functionally create an endoscope with single or multiple channels that run through its length.

In accordance with another embodiment of the present invention, instrument 46 or gastrointestinal tool 12 comprises a cutting tool or a sampling device for performing a variety of medical procedures, such as, but not limited to, removing polyps, performing sutures, irrigation, suction, and removing other tissues. Alternatively or additionally, gastrointestinal tool 12 may comprise a sensor for characterization of tissue, for example, for performing optical biopsy or chromoendoscopy (which relates to the spraying or injecting of a dye that is differentially accumulated by malignant tissue).

In accordance with an embodiment of the present invention, gastrointestinal tool 12 comprises a magnetic device, such as for coupling with other GI devices. For example, the magnetic device may be used to magnetically attract magnetic boluses or other ingestible objects used for tracking or imaging the GI tract. Alternatively, gastrointestinal tool 12 comprises any other suitable attachment or attraction device, such as but not limited to, adhesives or fasteners for attracting and affixing to such boluses or other ingestible objects.

In accordance with an embodiment of the present invention, substances are introduced in the GI tract via gastrointestinal tool 12 and or guiding element 16. Such substances may include, without limitation, materials injected for image contrast or labeling, such as, but not limited to, x-ray dyes, radioactivity-tagged materials or radiopharmaceuticals, magnetic resonance imaging (MRI) contrast agents, and others, or pharmaceuticals, relaxants, and other medicinal substances. Alternatively or additionally, a fluid (e.g., air) is introduced in the GI tract via gastrointestinal tool 12 and or guiding element 16 for inflating the colon. Such inflation of the colon typically enhances capturing images thereof, and/or enhances the local injection of pharmaceutical compounds (e.g., only to the colon), such as for the treatment of colitis and/or Crohn's disease.

In accordance with an embodiment of the present invention, guiding element 16 is advanced to a vicinity of the furthest desired location of gastrointestinal tool 12 in the colon (typically, but not necessarily, to the cecum), and, subsequently, tool 12 is advanced along guiding element 16 to the vicinity of the desired location.

The present invention thus provides a unique way of constructing gastrointestinal apparatus by advancing gastrointestinal tool 12 along (e.g., over or alongside) guiding element 16. Subsequently other tools may be slid over guiding element 16 to cooperate with gastrointestinal tool 12. As mentioned before, a collapsible sleeve (e.g., which may take the form of catheter 42 shown in FIG. 3) may be slid over guiding element 16 and inflated to functionally create an endoscope with single or multiple channels (e.g., 44 or 48) that run through its entire or partial length.

Figure 4:
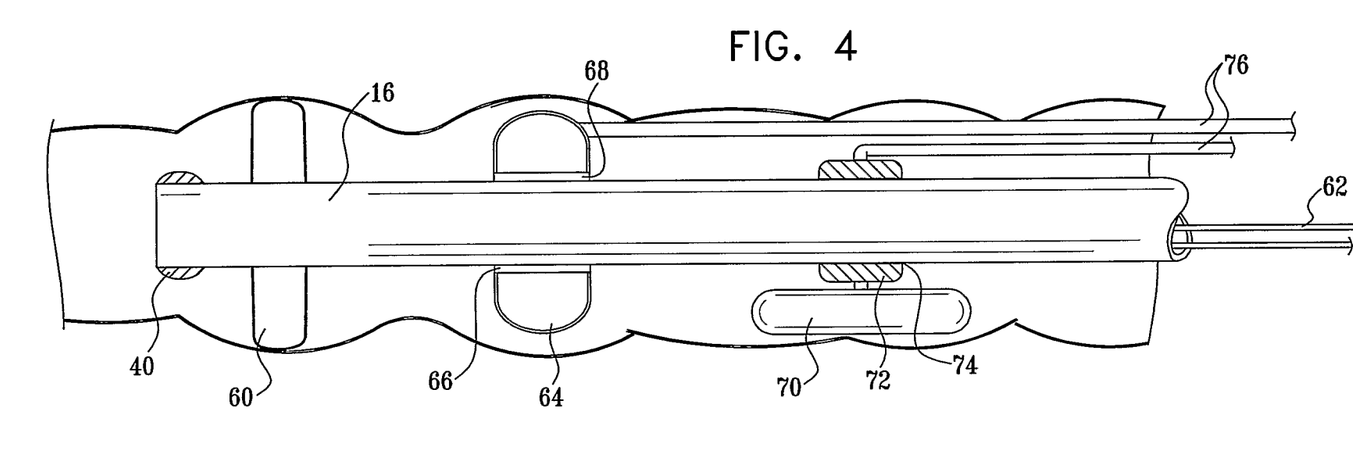
FIG. 4 is a simplified illustration of a gastrointestinal tool slid over the guiding element of FIG. 1, in accordance with an embodiment of the present invention.

Reference is now made to FIG. 4, which is a simplified schematic illustration of various gastrointestinal tools advanced along guiding element 16, in accordance with an embodiment of the present invention. In the illustrated embodiment, an anchoring device 60 is provided to anchor guiding element 16 at any desired position in the GI tract. The anchoring device 60 may be a balloon inflatable by means of pressurized gas or liquid introduced through a lumen 62 in fluid communication with the balloon. For some applications, guiding element 16 is anchored in order to facilitate a treatment or diagnosis, and or to facilitate movement of various components up and down the guiding element (e.g., monorail), by preventing longitudinal force from dislodging the guiding element (e.g., monorail) from its location. In an embodiment, anchoring device 60 comprises the inflatable piston head described hereinabove.

Different kinds of gastrointestinal tools may be slid over guiding element 16, as mentioned hereinabove. Two examples of possible configurations of such tools are shown in FIG. 4, in accordance with respective embodiments of the present invention. In one configuration, a gastrointestinal tool 64 comprises a coupling member 66 positioned inwards of the outer contour of gastrointestinal tool 64. Coupling member 66 may be a sleeve or disc, for example, formed with a bore 68. Guiding element 16 passes through bore 68. In another configuration, a gastrointestinal tool 70 comprises a coupling member 72 positioned outside the outer contour of gastrointestinal tool 70. Coupling member 72 may be an eyelet or small tube attached to the body of the gastrointestinal tool 70. Coupling member 72 may be formed with a bore 74 through which guiding element 16 passes. In such a case, guiding element 16 acts as a "monorail" with the gastrointestinal tool 70 gliding along it like a cable car. In the second configuration, the gastrointestinal tool 70 may comprise a capsule or colonoscope, for example.

There are many kinds of gastrointestinal tools that may be configured in either of the two configurations just described. (The tools are shown schematically and simplistically in FIG. 4, and it is noted that the shape and size of the tools may not be as exactly shown in the figure.) Some non-limiting examples of such gastrointestinal tools include a radioactive device (e.g., a radioactive tube, radioactive needle, radioactive seed, and/or radioactive capsule or combination thereof), or an iontophoresis drug delivery device. The iontophoresis drug delivery device may comprise at least two electrodes in intimate electrical contact with some portion of the GI tract, wherein one electrode is the active or donor electrode, from which an ionic substance, agent, medicament, drug precursor or drug is delivered into the body via the wall of the GI tract by iontophoresis.

The other electrode, called the counter or return electrode, serves to close the electrical circuit through the body. The circuit is completed by connection of the electrodes to a source of electrical energy, e.g., a battery. One or both of the anode and the cathode may be used to deliver drugs of appropriate charge into the body.

Other non-limiting examples of such gastrointestinal tools include an imaging device (e.g., miniature CCD or x-ray imaging device), a miniature injection device for injection of a substance (e.g., an endoscopically-actuated injection needle and/or syringe), a photodynamic therapy/diagnosis device (e.g., an LED-based light infusion device), a hyperthermic therapy/diagnosis device (e.g., miniature high frequency ultrashort wave electrodes), or an ultrasonic therapy/diagnosis device (e.g., miniature ultrasound transducer). The imaging or viewing device may be used to position the gastrointestinal tool at any desired position along guiding element 16.

In the case of diagnostic applications, energy, such as ultrasonic or x-ray energy, is applied to at least a portion of the GI tract to image the target tissue. A visible image of an internal region of the GI tract is then obtained, such that the presence or absence of diseased tissue can be ascertained. With respect to ultrasound, ultrasonic imaging techniques, including second harmonic imaging, and gated imaging, are well known in the art. Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Diagnostic ultrasound generally involves the application of a pulse of echoes, after which, during a listening period, the ultrasound transducer receives reflected signals. Harmonics, ultra-harmonics or subharmonics may be used. Energy levels for therapeutic ultrasound may be used to perform hyperthermia.

Photodynamic therapy/diagnosis utilizes the administration of a light-sensitive drug, which is then exposed to a visible light beam, which, in the case of therapy, may destroy cancerous cells. It is known that certain dyes are accreted by lesions, such as tumors, which are in turn activated by a specific frequency of light. The photodynamic therapy/diagnosis device may employ laser-induced fluorescence to detect sites of cancer which have accreted the light-activated dye. Fluorescent and other chromagens, or dyes, such as porphyrins sensitive to visible light, have been used to detect and even treat lesions by directing the suitable light to the tumor or lesion. Other synonymous names for photodynamic therapy/diagnosis device include photoradiation and phototherapy.

Another gastrointestinal tool may include a dye applicator, which may be used to coat, paint, spray or otherwise apply a color, pigment, dye or other highlighting substance on the inner walls of the GI tract. In this manner, polyps or other growths or anomalies may be highlighted so that they are more easily discerned and imaged by the colonoscope. This may also aid in pattern recognition of tissue in the colon by the colonoscope, so as to facilitate analysis by the colonoscope. This may also enable placement of a landmark to facilitate returning the colonoscope to the same location in the colon. It is also noted that certain polyps or other growths may react differently to the addition of the dye, such as in terms of color change, absorption, etc., and the reaction of the growth may be correlated to its probability of turning into a cancerous growth. Optical biopsy techniques that may be used include, but are not limited to, confocal microendoscopy, fluorescence endoscopy, optical coherence tomography, light-scattering spectroscopy, Raman spectroscopy, and molecular imaging. For some applications, optical biopsy facilitates the performance of histological analysis of tissue of the colon.

A propulsion device 76 may be provided to propel (e.g., push or pull) the gastrointestinal tool along guiding element 16. For example, the propulsion device 76 may include a push and/or pull wire attached to the tool. In another non-limiting example, the propulsion device 76 may include a jet-propulsion device that moves the tool distally over guiding element 16 by means of a jet of water or air expelled proximally from the jet-propulsion device. As another example, the propulsion device 76 may be a motor with gearing which may not need any external connections, which moves the gastrointestinal tool along guiding element 16.

Figure 5:
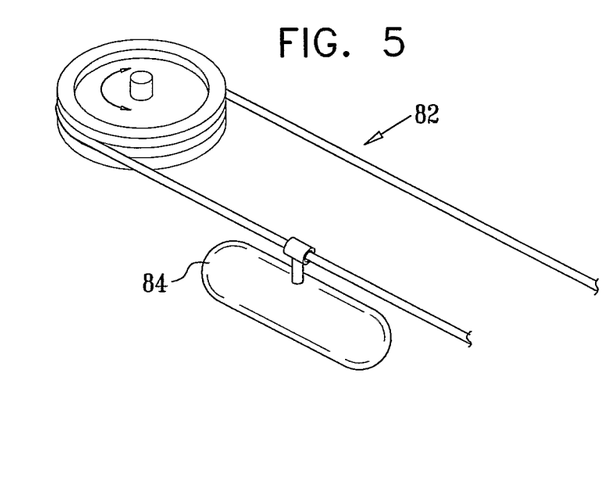
FIG. 5 is a simplified illustration of a gastrointestinal tool with a pulley for movement over the guiding element of FIG. 1, in accordance with an embodiment of the present invention.

Reference is now made to FIG. 5, which illustrates a gastrointestinal tool 80 with another kind of propulsion device, in accordance with an embodiment of the present invention. In this embodiment, the propulsion device includes a pulley 82 for movement over guiding element 16. A gastrointestinal tool 84 may be coupled to pulley 82 and moved distally and/or proximally along guiding element 16. The pulley 82 may be connected to the end of guiding element 16 or any other portion thereof, or to any other device that moves along or with the catheter (the catheter being guiding element 16).

Figure 6:
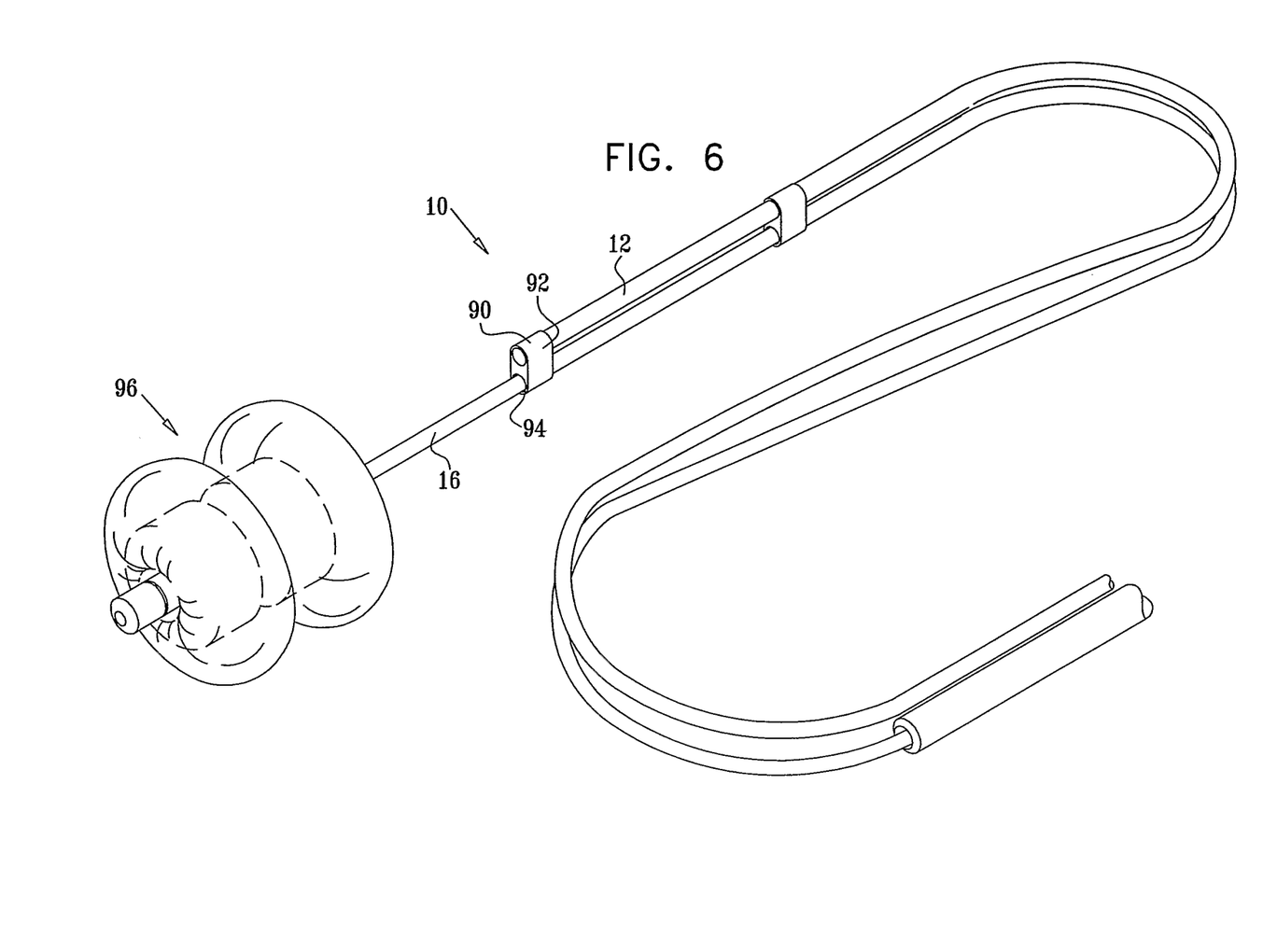
FIG. 6 is a schematic illustration of a configuration of the guiding element of FIG. 1, in accordance with an embodiment of the present invention.

Reference is now made to FIG. 6, which is a schematic illustration of a configuration of gastrointestinal device 10, in accordance with an embodiment of the present invention. In this configuration, gastrointestinal tool 12 is not formed with a bore, such as described hereinabove with reference to FIGS. 1 and 2. Instead, tool 12 comprises a coupling member 90, a tool-coupling portion 92 of which is typically fixed (i.e., non-slidably coupled) to tool 12. Coupling member 90 is shaped so as to define a bore 94 through a portion of the coupling member, such that bore 94 is positioned adjacent to tool 12. Guiding element 16 is configured to pass through bore 94, such that tool 12 advances alongside guiding element 16. For some applications, gastrointestinal device 10 comprises a mechanical device 96, for example as described hereinabove and/or in the above-mentioned U.S. patent application Ser. No. 10/967,922 to Cabiri et al. For some applications, mechanical device 96 comprises a multi-lobed piston head, as shown in FIG. 6, similar to the configuration described with reference to FIGS. 10A-1 1B of the Cabiri et al. application. Alternatively, for some applications, mechanical device 96 comprises a single-lobed piston head (configuration not shown in FIG. 6).

Figure 7:
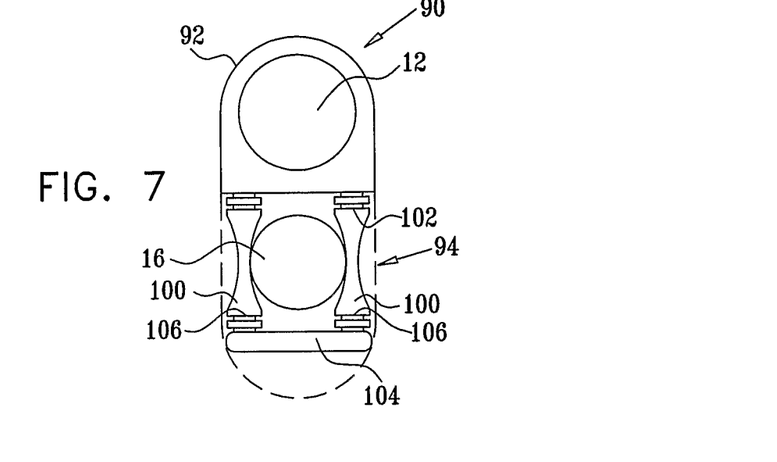
FIG. 7 is a schematic cross-sectional view of a configuration of a bore of the guiding element of FIG. 6, in accordance with an embodiment of the present invention.

FIG. 7 is a schematic cross-sectional view of a configuration of bore 94 of coupling member 90, in accordance with an embodiment of the present invention. In this configuration, coupling member 90 comprises one or more (e.g., two) wheels 100, typically coupled at first ends 102 thereof to tool-coupling portion 92. Wheels 100 are disposed so as to define bore 94 therebetween. In the configuration shown in FIG. 7, wheels 100 are driven to rotate in opposite directions, in order to force guiding element 16 to pass between the wheels, and thereby cause tool 12 to advance along guiding element 16. As appropriate, wheels 100 may be driven electrically, pneumatically, or hydraulically. For some applications, coupling member 90 comprises a retaining element 104 coupled to second ends 106 of wheels 100. Retaining element 104 prevents guiding element 16 from becoming disengaged from bore 94, and/or maintains the wheels in alignment with each other. In an embodiment, guiding element 16 is flexible, has a diameter greater than about 4 mm (e.g., about 5.5 mm), and is slightly transiently deformed by pressure applied thereto by wheels 100. For example, the guiding element may comprise polyurethane.

Figure 8A:
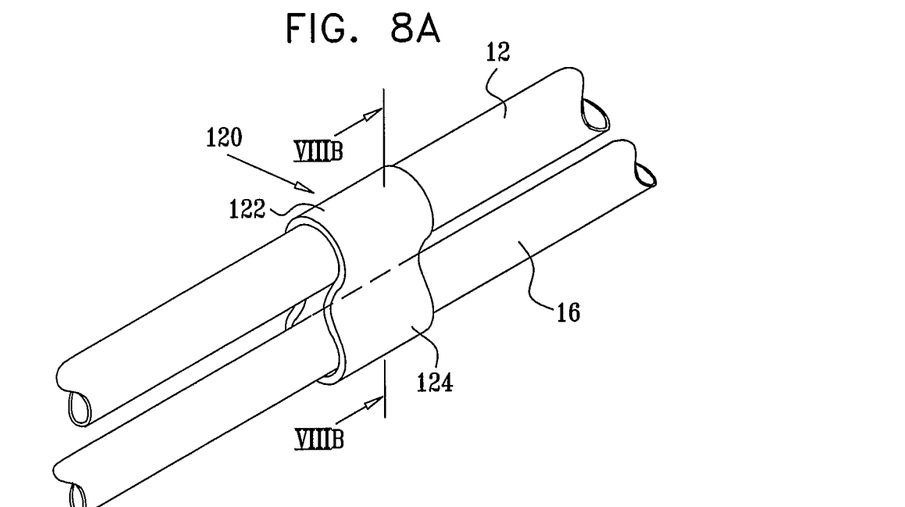
FIGS. 8A and 8B are schematic side and cross-sectional views, respectively, of a clip for use with a guiding element, in accordance with an embodiment of the present invention.
Figure 8B:
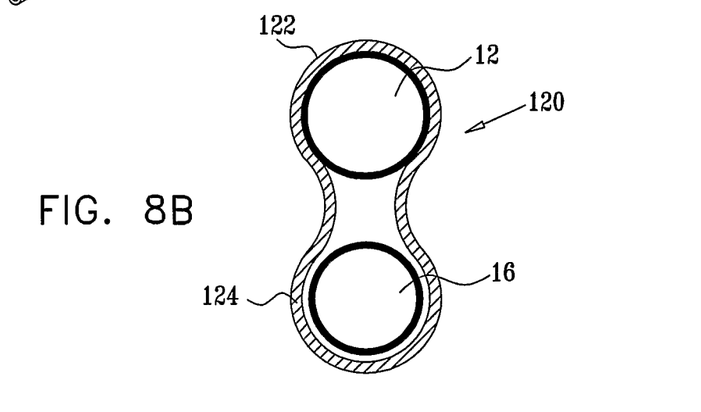

FIGS. 8A and 8B are schematic side and cross-sectional views, respectively, of a clip 120, in accordance with an embodiment of the present invention. For some applications, gastrointestinal device 10 comprises one or more clips 120, which serve to slidably couple guiding element 16 to tool 12 along at least a longitudinal portion of the guiding element. Typically, a first portion 122 of clip 120 is fixed (i.e., non-slidably coupled) to tool 12, and a second portion 124 of clip 120 is slidably coupled to guiding element 16. For some applications, clip 120 comprises the wheel configuration described hereinabove with reference to FIG. 7, but the wheels rotate passively.

Some embodiments of the present invention are described hereinabove with respect to the use of an inflatable device to pull a guiding element. It is noted that this description is by way of illustration and not limitation. The scope of the present invention includes the use of other devices, as well. For example, a magnetically-driven device may be used to pull the guiding element. Alternatively, a non-magnetically-driven device may be used to pull the guiding element. Typically, but not necessarily, the non-magnetically-driven device generates an overall mechanical force that is generally in line with an axis of the lumen through which it travels. Thus, movement of the non-magnetically-driven device generally does not, in and of itself, cause any substantial distortion of the direction of the lumen. As appropriate, the non-magnetically-driven device may comprise a device such as an electromechanical device, a mechanical device, or a device that uses suction to facilitate its advancement (e.g., as are known in the art).

For some applications, techniques described herein are used in combination with techniques described in one or more of the following applications, all of which are assigned to the assignee of the present application and are incorporated herein by reference:

U.S. patent application Ser. No. 10/967,922 to Cabiri et al., filed Oct. 18, 2004, entitled, "Pressure-propelled system for body lumen,"

U.S. patent application Ser. No. 10/838,648 to Gross et al., filed May 3, 2004, entitled, "Pressure-propelled system for body lumen,"

U.S. patent application Ser. No. 10/753,424 to Gross et al., filed Jan. 9, 2004, entitled, "Pressure-propelled system for body lumen,"

U.S. Provisional Patent Application 60/607,986 to Cabiri et al., filed Sep. 8, 2004, entitled, "Mechanical aspects of pressure-propelled system for body lumen," and U.S. Provisional Patent Application 60/571,438 to Dotan et al., filed May 14, 2004, entitled, "Omnidirectional and forward-looking imaging device."

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

The invention claimed is:

1. A gastrointestinal apparatus comprising:
a guiding element carrying an inflatable mechanical gastrointestinal device and a gastrointestinal tool adapted to be advanced along the guiding element, said guiding element configured to be introduced through a return into a colon of a patient;
a piston head coupled to the guiding element;
a pressure generating means for generating fluid pressure in the colon when said guiding element is introduced into the colon;
a vent tube shaped so as to define an opening distal to the piston head to facilitate passage of fluid out of the colon from a site distal to the piston head; and
a guide member for being at least partially insertable into a proximal opening of said colon, the guide member being formed with a passageway connectable to said pressure generating means and for conveying the fluid pressure into the colon for inflating the colon when the guide member is inserted into the colon, and applying the fluid pressure on an external surface of the piston head;
the gastrointestinal apparatus being configured to facilitate distal advancement of the piston head by facilitating passage of fluid out of the colon from a distal site within the colon distal to the piston head via the vent tube, and said piston head being configured to be inflated so as to form a pressure seal with a wall of the colon, and to be advanced distally due to the fluid pressure applied over an external surface of the piston head, whereby greater fluid pressure acts on a proximal side of the piston head than on a distal side of the piston head.

2. The gastrointestinal apparatus according to claim 1, wherein the guiding element comprises a distal stop that prevents movement of the gastrointestinal tool therepast.

3. The gastrointestinal apparatus according; to claim, wherein the gastrointestinal tool is shaped to define a chamfer for facilitating passage through a lumen.

4. The gastrointestinal apparatus according to claim 1, wherein the gastrointestinal tool comprises a cutting tool.

5. The gastrointestinal apparatus according to claim 1, wherein the gastrointestinal tool comprises a sampling device.

6. The gastrointestinal apparatus according to claim 1, wherein gastrointestinal tool comprises a magnetic device.

7. The gastrointestinal apparatus according to claim 1, wherein the guiding element has a diameter of at least 4 mm.

8. The gastrointestinal apparatus according to claim 1, wherein the gastrointestinal tool comprises an imaging device.

9. The gastrointestinal apparatus according to claim 8, wherein the imaging device comprises a CCD camera, a CMOS camera, an illumination device, a vision device, an ultrasound sensor, or an x-ray emitter.

10. The gastrointestinal apparatus according to claim 1, wherein the gastrointestinal tool comprises a catheter that slides over the guiding element.

11. The gastrointestinal apparatus according to claim 10, wherein the catheter comprises a lumen for passing therethrough an instrument or as fluid.

12. The gastrointestinal apparatus according to claim 1, wherein the piston head is adapted to be in direct contact with the wall of the colon when the guiding element is in the colon.

13. The gastrointestinal apparatus according to claim 1, wherein the piston head is shaped to define a proximal lobe and a distal lobe, the lobes being in fluid communication with each other.

14. The gastrointestinal apparatus according to claim 1, wherein the vent tube is adapted to passively permit the passage of the fluid out of the colon from the distal site within the colon.

15. The gastrointestinal apparatus according to claim 1, wherein the vent tube is adapted to be coupled to a suction source, whereby to actively facilitate the passage of the fluid out of the colon from the distal site within the colon.

16. The gastrointestinal apparatus according to claim 1, wherein the gastrointestinal tool comprises a coupling member shaped to define a bore, the guiding element passing through the bore.

17. The gastrointestinal apparatus according to claim 16, wherein the coupling member is positioned inwards of an outer contour of the gastrointestinal tool.

18. The gastrointestinal apparatus according to claim 16, wherein the coupling member is positioned outside an outer contour of the gastrointestinal tool.

19. The gastrointestinal apparatus according to claim 1, wherein the gastrointestinal tool comprises a radioactive tube, a radioactive needle, radioactive seed, or a radioactive capsule.

20. The gastrointestinal apparatus according to claim 1, wherein the gastrointestinal tool comprises an iontophoresis drug delivery device.

21. The gastrointestinal apparatus according to claim 1, wherein the gastrointestinal tool comprises an injection device for injection of a substance.

22. The gastrointestinal apparatus according to claim 1, wherein the gastrointestinal tool comprises a photodynamic therapy/diagnosis device.

23. The gastrointestinal apparatus according to claim 1, wherein the gastrointestinal tool comprises a hyperthermic therapy/diagnosis device.

24. The gastrointestinal apparatus according to claim 1, wherein the gastrointestinal tool comprises an ultrasonic therapy/diagnosis device.

25. The gastrointestinal apparatus according to claim 1, wherein the gastrointestinal tool comprises an optical biopsy device.

26. The gastrointestinal apparatus according to claim 1, comprising one or more clips, adapted to be clipped to the guiding element and the gastrointestinal tool, to facilitate sliding of the tool with respect to the guiding element.

27. The gastrointestinal apparatus according to claim 1, wherein the gastrointestinal tool is adapted to be actively advanced along the guiding element.

28. The gastrointestinal apparatus according to claim 1, further comprising an anchoring device adapted to anchor the guiding element at a position in a gastrointestinal tract.

29. The gastrointestinal apparatus according to claim 28, wherein the anchoring device comprises an inflatable balloon.

30. The gastrointestinal apparatus according to claim 1, wherein the vent tube passes through the piston head.

* * * * *

UNITED STATES PATENT AND TRADEMARK OFFICE
CERTIFICATE OF CORRECTION

| | | |
|---|---|---|
| PATENT NO. | : 8,602,974 B2 | Page 1 of 1 |
| APPLICATION NO. | : 11/813457 | |
| DATED | : December 10, 2013 | |
| INVENTOR(S) | : Benad Goldwasser et al. | |

It is certified that error appears in the above-identified patent and that said Letters Patent is hereby corrected as shown below:

In the Claims:

At column 15, claim number 3, at the end of line number 60, after "claim," please insert the number --1--.

Signed and Sealed this
Eighteenth Day of February, 2014

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,602,974 B2 |
| APPLICATION NO. | : 11/813457 |
| DATED | : December 10, 2013 |
| INVENTOR(S) | : Benad Goldwasser et al. |

It is certified that error appears in the above-identified patent and that said Letters Patent is hereby corrected as shown below:

In the Claims:

At column 15, claim number 1, at the end of line number 31, please change "return" to --rectum--.

At column 16, claim number 6, at the beginning of line 2, after "wherein," please insert --the--.

Signed and Sealed this
Second Day of September, 2014

Michelle K. Lee
*Deputy Director of the United States Patent and Trademark Office*